(12) United States Patent
Surti et al.

(10) Patent No.: US 8,377,095 B2
(45) Date of Patent: Feb. 19, 2013

(54) TISSUE ANCHORS FOR PURSE-STRING CLOSURE OF PERFORATIONS

(75) Inventors: Vihar C. Surti, Winston-Salem, NC (US); Richard W. Ducharme, Winston-Salem, NC (US)

(73) Assignee: Cook Medical Technologies, LLC, Bloomington, IN (US)

( * ) Notice: Subject to any disclaimer, the term of this patent is extended or adjusted under 35 U.S.C. 154(b) by 467 days.

(21) Appl. No.: 12/630,395

(22) Filed: Dec. 3, 2009

(65) Prior Publication Data

US 2010/0145385 A1    Jun. 10, 2010

Related U.S. Application Data

(60) Provisional application No. 61/120,220, filed on Dec. 5, 2008.

(51) Int. Cl.
*A61B 17/04* (2006.01)
(52) U.S. Cl. .......... 606/232; 606/151; 24/128; 24/129 R
(58) Field of Classification Search ............ 606/74, 606/103, 139, 142–158, 232, 300; 24/128, 24/129 R, 131 R, 712.1, 712.2
See application file for complete search history.

(56) References Cited

U.S. PATENT DOCUMENTS

| | | | |
|---|---|---|---|
| 2,199,025 A | 4/1940 | Conn | |
| 2,595,806 A * | 5/1952 | Morris | 24/129 R |
| 3,556,079 A | 1/1971 | Omizo | |
| 4,235,238 A | 11/1980 | Ogiu et al. | |
| 4,669,473 A * | 6/1987 | Richards et al. | 606/215 |
| 4,823,794 A * | 4/1989 | Pierce | 606/232 |
| 4,918,785 A * | 4/1990 | Spinner et al. | 16/428 |
| 5,123,914 A | 6/1992 | Cope | |
| 5,203,787 A | 4/1993 | Noblitt et al. | |
| 5,333,624 A | 8/1994 | Tovey | |
| 5,366,480 A | 11/1994 | Corriveau et al. | |
| 5,417,691 A | 5/1995 | Hayhurst | |
| 5,520,700 A | 5/1996 | Beyar et al. | |
| 5,527,343 A | 6/1996 | Bonutti | |
| 5,554,183 A | 9/1996 | Nazari | |
| 5,662,683 A | 9/1997 | Kay | |
| 5,690,656 A | 11/1997 | Cope et al. | |
| 5,693,060 A * | 12/1997 | Martin | 606/148 |
| 5,810,848 A | 9/1998 | Hayhurst | |
| 5,865,791 A | 2/1999 | Whayne et al. | |
| 5,891,159 A | 4/1999 | Sherman et al. | |
| 5,941,900 A * | 8/1999 | Bonutti | 606/232 |

(Continued)

FOREIGN PATENT DOCUMENTS

| | | |
|---|---|---|
| EP | 0774237 A2 | 5/1997 |
| EP | 1484021 A1 | 12/2004 |

(Continued)

OTHER PUBLICATIONS

International Search Report & Written Opinion (Jul. 31, 2008) PCT/US2007/085769.

(Continued)

*Primary Examiner* — Corrine M McDermott
*Assistant Examiner* — Mark Mashack
(74) *Attorney, Agent, or Firm* — Brinks Hofer Gilson & Lione

(57) ABSTRACT

Medical devices for attaching suture to tissue and that provides reliable and complete closure of perforations and increases the versatility of the device for various other procedures. Embodiments of the medicals devices include a tissue anchor having a crossbar with opposing ends and structure for slidably receiving a suture.

12 Claims, 4 Drawing Sheets

U.S. PATENT DOCUMENTS

| | | | | |
|---|---|---|---|---|
| 5,968,078 | A | 10/1999 | Grotz | |
| 5,987,707 | A * | 11/1999 | DeShon | 24/17 AP |
| 6,030,007 | A * | 2/2000 | Bassily et al. | 289/1.5 |
| 6,110,183 | A | 8/2000 | Cope | |
| RE36,974 | E | 11/2000 | Bonutti | |
| 6,257,163 | B1 * | 7/2001 | Carpenter | 114/253 |
| 6,290,674 | B1 | 9/2001 | Roue et al. | |
| 6,328,727 | B1 | 12/2001 | Frazier et al. | |
| 6,419,669 | B1 | 7/2002 | Frazier et al. | |
| 6,423,087 | B1 | 7/2002 | Sawada | |
| 6,482,178 | B1 | 11/2002 | Andrews et al. | |
| 6,491,707 | B2 | 12/2002 | Makower et al. | |
| 6,551,333 | B2 | 4/2003 | Kuhns et al. | |
| 6,572,629 | B2 | 6/2003 | Kalloo et al. | |
| 6,592,559 | B1 | 7/2003 | Pakter et al. | |
| 6,641,557 | B1 | 11/2003 | Frazier et al. | |
| 6,652,563 | B2 * | 11/2003 | Dreyfuss | 606/232 |
| 6,699,263 | B2 | 3/2004 | Cope | |
| 6,712,804 | B2 | 3/2004 | Roue et al. | |
| 6,746,472 | B2 | 6/2004 | Frazier et al. | |
| 6,966,916 | B2 | 11/2005 | Kumar | |
| 6,972,027 | B2 | 12/2005 | Fallin et al. | |
| 7,025,756 | B2 | 4/2006 | Frazier et al. | |
| 7,056,325 | B1 | 6/2006 | Makower et al. | |
| 7,076,845 | B2 * | 7/2006 | Tylaska et al. | 24/135 N |
| 7,087,073 | B2 | 8/2006 | Bonutti | |
| 7,115,110 | B2 | 10/2006 | Frazier et al. | |
| 7,217,279 | B2 | 5/2007 | Reese | |
| RE39,841 | E | 9/2007 | Bilotti | |
| 7,326,231 | B2 | 2/2008 | Phillips et al. | |
| RE40,237 | E | 4/2008 | Bilotti et al. | |
| 7,390,329 | B2 | 6/2008 | Westra et al. | |
| 7,416,554 | B2 | 8/2008 | Lam et al. | |
| 7,494,496 | B2 | 2/2009 | Swain et al. | |
| 7,601,159 | B2 | 10/2009 | Ewers et al. | |
| 7,618,426 | B2 | 11/2009 | Ewers et al. | |
| 7,621,925 | B2 | 11/2009 | Saadat et al. | |
| 7,622,068 | B2 | 11/2009 | Li et al. | |
| 7,641,836 | B2 | 1/2010 | Li et al. | |
| 7,674,275 | B2 | 3/2010 | Martin et al. | |
| 7,678,135 | B2 | 3/2010 | Maahs et al. | |
| 7,691,112 | B2 * | 4/2010 | Chanduszko et al. | 606/139 |
| 7,695,493 | B2 | 4/2010 | Saadat et al. | |
| 7,704,264 | B2 | 4/2010 | Ewers et al. | |
| 7,736,376 | B2 | 6/2010 | Sato et al. | |
| 7,736,378 | B2 | 6/2010 | Maahs et al. | |
| 7,736,379 | B2 | 6/2010 | Ewers et al. | |
| 7,744,613 | B2 | 6/2010 | Ewers et al. | |
| 7,758,598 | B2 | 7/2010 | Conlon et al. | |
| 7,780,702 | B2 | 8/2010 | Shiono | |
| 7,815,659 | B2 | 10/2010 | Conlon et al. | |
| 7,815,662 | B2 | 10/2010 | Spivey et al. | |
| 2004/0147941 | A1 | 7/2004 | Takemoto et al. | |
| 2004/0147958 | A1 * | 7/2004 | Lam et al. | 606/232 |
| 2004/0220596 | A1 | 11/2004 | Frazier et al. | |
| 2004/0243179 | A1 | 12/2004 | Foerster | |
| 2005/0143762 | A1 | 6/2005 | Paraschac et al. | |
| 2005/0149067 | A1 | 7/2005 | Takemoto et al. | |
| 2005/0171562 | A1 | 8/2005 | Criscuolo et al. | |
| 2005/0197594 | A1 | 9/2005 | Burbank et al. | |
| 2005/0234512 | A1 * | 10/2005 | Nakao | 606/232 |
| 2005/0251166 | A1 | 11/2005 | Vaughan et al. | |
| 2005/0277957 | A1 | 12/2005 | Kuhns et al. | |
| 2006/0002852 | A1 | 1/2006 | Saltzman et al. | |
| 2006/0004409 | A1 | 1/2006 | Nobis et al. | |
| 2006/0004410 | A1 | 1/2006 | Nobis et al. | |
| 2006/0015006 | A1 | 1/2006 | Laurence et al. | |
| 2006/0020274 | A1 | 1/2006 | Ewers et al. | |
| 2006/0020277 | A1 | 1/2006 | Gostout et al. | |
| 2006/0135989 | A1 | 6/2006 | Carley et al. | |
| 2006/0190016 | A1 | 8/2006 | Onuki et al. | |
| 2006/0206063 | A1 | 9/2006 | Kagan et al. | |
| 2006/0217762 | A1 | 9/2006 | Maahs et al. | |
| 2006/0235447 | A1 | 10/2006 | Walshe | |
| 2006/0237022 | A1 | 10/2006 | Chen et al. | |
| 2006/0241691 | A1 | 10/2006 | Wilk | |
| 2006/0265010 | A1 | 11/2006 | Paraschac et al. | |
| 2007/0010835 | A1 | 1/2007 | Breton et al. | |
| 2007/0049970 | A1 | 3/2007 | Belef et al. | |
| 2007/0093858 | A1 | 4/2007 | Gambale et al. | |
| 2007/0100375 | A1 | 5/2007 | Mikkaichi et al. | |
| 2007/0112425 | A1 * | 5/2007 | Schaller et al. | 623/2.37 |
| 2007/0150003 | A1 * | 6/2007 | Dreyfuss et al. | 606/232 |
| 2007/0162052 | A1 | 7/2007 | Hashimoto et al. | |
| 2007/0208360 | A1 * | 9/2007 | Demarais et al. | 606/153 |
| 2007/0213702 | A1 | 9/2007 | Kogasaka et al. | |
| 2007/0255317 | A1 * | 11/2007 | Fanton et al. | 606/232 |
| 2007/0270752 | A1 | 11/2007 | LaBombard | |
| 2007/0270889 | A1 | 11/2007 | Conlon et al. | |
| 2007/0276416 | A1 | 11/2007 | Ginn et al. | |
| 2007/0276424 | A1 | 11/2007 | Mikkaichi et al. | |
| 2008/0065157 | A1 | 3/2008 | Crombie et al. | |
| 2008/0114398 | A1 | 5/2008 | Phillips et al. | |
| 2008/0154290 | A1 | 6/2008 | Golden et al. | |
| 2008/0172088 | A1 | 7/2008 | Smith et al. | |
| 2008/0185752 | A1 | 8/2008 | Cerwin et al. | |
| 2008/0200930 | A1 | 8/2008 | Saadat et al. | |
| 2008/0208214 | A1 | 8/2008 | Sato et al. | |
| 2008/0208218 | A1 | 8/2008 | Shiono | |
| 2008/0208219 | A1 | 8/2008 | Suzuki | |
| 2008/0208251 | A1 | 8/2008 | Weadock et al. | |
| 2008/0228202 | A1 | 9/2008 | Cropper et al. | |
| 2008/0228253 | A1 | 9/2008 | Bell et al. | |
| 2008/0243148 | A1 | 10/2008 | Mikkaichi et al. | |
| 2008/0255422 | A1 | 10/2008 | Kondoh et al. | |
| 2008/0255427 | A1 | 10/2008 | Satake et al. | |
| 2008/0269566 | A1 | 10/2008 | Measamer | |
| 2008/0296344 | A1 | 12/2008 | Cropper et al. | |
| 2008/0300627 | A1 | 12/2008 | Measamer et al. | |
| 2008/0300629 | A1 | 12/2008 | Surti | |
| 2008/0319257 | A1 | 12/2008 | Sato et al. | |
| 2009/0005800 | A1 | 1/2009 | Franer et al. | |
| 2009/0024163 | A1 | 1/2009 | Zeiner et al. | |
| 2009/0076527 | A1 | 3/2009 | Miyamoto et al. | |
| 2009/0088780 | A1 | 4/2009 | Shiono et al. | |
| 2009/0125039 | A1 | 5/2009 | Mikkaichi et al. | |
| 2009/0204146 | A1 * | 8/2009 | Kaiser et al. | 606/228 |
| 2009/0204147 | A1 | 8/2009 | Rahmani | |
| 2009/0299406 | A1 | 12/2009 | Swain et al. | |
| 2009/0326561 | A1 | 12/2009 | Carroll, II et al. | |
| 2009/0326578 | A1 | 12/2009 | Ewers et al. | |
| 2010/0010457 | A1 | 1/2010 | Ewers et al. | |
| 2010/0042115 | A1 | 2/2010 | Saadar et al. | |
| 2010/0042144 | A1 | 2/2010 | Bennett | |
| 2010/0076462 | A1 | 3/2010 | Bakos et al. | |
| 2010/0076488 | A1 | 3/2010 | Spivey et al. | |
| 2010/0094083 | A1 | 4/2010 | Taylor et al. | |
| 2010/0094341 | A1 | 4/2010 | Raju | |
| 2010/0106166 | A1 | 4/2010 | Cropper et al. | |
| 2010/0113873 | A1 | 5/2010 | Suzuki et al. | |
| 2010/0174312 | A1 | 7/2010 | Maahs et al. | |
| 2010/0198192 | A1 | 8/2010 | Serina et al. | |
| 2010/0211086 | A1 | 8/2010 | Ewers et al. | |
| 2010/0256679 | A1 | 10/2010 | Ducharme | |
| 2010/0268253 | A1 | 10/2010 | Ahlberg et al. | |
| 2011/0190815 | A1 * | 8/2011 | Saliman | 606/232 |
| 2012/0271331 | A1 * | 10/2012 | To et al. | 606/151 |

FOREIGN PATENT DOCUMENTS

| | | |
|---|---|---|
| EP | 1598018 A1 | 11/2005 |
| EP | 1602336 A1 | 12/2005 |
| EP | 1938760 A1 | 7/2008 |
| EP | 2042105 A1 | 4/2009 |
| WO | WO/ 01/10312 A1 | 2/2001 |
| WO | WO/0158363 | 8/2001 |
| WO | WO 2006/044837 A2 | 4/2006 |
| WO | WO 2008/067384 A2 | 6/2008 |
| WO | WO 2008/109087 A1 | 9/2008 |

OTHER PUBLICATIONS

International Preliminary Report on Patentablility (Jun. 3, 2009) PCT/US2007/085769.

International Search Report & Written Opinion (Jun. 6, 2010) PCT/US2010/029798.

International Search Report & Written Opinion (Mar. 5, 2010) PCT/US2009/066566.

Article 34 Amendment for PCT/US09/66566.

A. Fritscher-Ravens, Transgastric Endoscopy—A new Fashion, a New Excitement, Article pp. 161-167, Endoscopy 2007—vol. 39, Homerton Hospital, UK.

R.P. Voermans et al., In Vitro Comparison and Evaluation of Seven Gastric Closure Modalities for Natural Orifice Transluminal Endoscopic Surgery (NOTES), Article pp. 595-601, Endoscopy 2008, vol. 40.

Guido M. Sclabas, et al., Endoluminal Methods for Gastrotomy Closure in Natural Orifice TransEnteric Surgery (NOTES), Surgical Innovation, vol. 13, No. 1 pp. 23-30, Mar. 2006.

Emanuel Sporn, et al., Endoscopic Colotomy Closure for Natural Orifice Transluminal Endoscopic Surgery Using a T-Fastener Prototype in Comparison to Convential Laparoscopic Suture Closure, Article Gastrointestinal Endoscopy, pp. 724-730, vol. 68, No. 4, 2008.

David J. Desilets, et al., Loop-Anchor Purse-String Versus Endoscopic Clips for Gastric Closure: A Natural Orifice Transluminal Endoscopic Surgery Comparison Study Using Burst Pressures, Journal Gastrointestinal Endoscopy pp. 1225-1230, vol. 70, No. 6, 2009.

E. Sporn, et al., Endoscopic Colotomy Closure After Full Thickness Excision: Comparison of T Fastener with Multiclip Applier, Article Endoscopy, pp. 589-594, vol. 40 2008.

Maria Bergstrom, et al., Early Clinical Experience with a New Flexible Endoscopic Suturing Method for Natural Orifice Transluminal Endoscopic Surgery and Intraluminal Endosurgery, Article Gastrointestinal Endoscopy, pp. 528-533, vol. 67, No. 3, 2008.

Xavier Dray, et al. Air and Fluid Leak Tests after NOTES procedures: A Pilot Study in a Live Porcine Model, Article Gastrointestinal Endoscopy, pp. 513-519, vol. 68, No. 3, 2008.

P.O. Park, et al., Endoscopic Sutured Closure of a Gastric Natural Orifice Transluminal Endoscopic Surgery Access Gastrotomy Compared with open Surgical Closure in a Porcine Model. A Randomized, Multicenter Controlled Trial, Article Endoscopy 2010, vol. 42, pp. 311-317.

* cited by examiner

TISSUE ANCHORS FOR PURSE-STRING CLOSURE OF PERFORATIONS

CROSS-REFERENCE TO RELATED APPLICATIONS

This application claims the benefit of U.S. Provisional Application Ser. No. 61/120,220 filed on Dec. 5, 2008, entitled "TISSUE ANCHORS FOR PURSE-STRING CLOSURE OF PERFORATIONS" the entire contents of which are incorporated herein by reference.

FIELD

The present invention relates generally to tissue anchors for connecting a suture to tissue, such are for using tissue anchors and suture to close perforations in tissue.

BACKGROUND

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors (T-anchors) or visceral anchors. An exemplary tissue anchor is disclosed in U.S. Pat. No. 5,123,914, the entire contents of which are incorporated by reference herein. Such tissue anchors have been very successful in medical procedures requiring tissue wall mobilization or wall apposition.

Tissue anchors have also been successfully used in closing perforations, but are not without their drawbacks. For example, when a series of anchors are placed around a perforation, all of the individual sutures connected to the anchors must be collected and connected together. It can often be difficult to properly tension each of the individual sutures to ensure proper approximation of the tissue around the perforation and complete closure thereof. This is especially critical within the gastrointestinal tract, where the travel of bacteria laden fluids outside of the tract may cause unwanted and sometimes deadly infection.

BRIEF SUMMARY

The present invention provides medical devices for attaching suture to tissue and that provides reliable and complete closure of perforations and increases the versatility of the device for various other procedures. One embodiment of a tissue anchor for connecting a suture to tissue, constructed in accordance with the teachings of the present invention, generally comprises a crossbar and a strand. The crossbar has first and second opposing ends and defines a longitudinal axis. The crossbar is defined by a tubular wall having an aperture between the first and second ends. The strand has first and second opposing ends connected to the first and second opposing ends of the crossbar, respectively. The strand makes a revolution to define a loop. The strand and its loop project through the aperture and away from the longitudinal axis. The loop is sized to slidably receive the suture therethrough.

According to more detailed aspects of this embodiment of the tissue anchor, the strand has a diameter less than about 50% of a diameter of the crossbar. The strand preferably has a diameter in the range of about 0.2 mm to about 0.35 mm, while the crossbar has a diameter in the range of about 0.5 mm to about 1.1 mm. The loop has an apex located about 0.35 mm or greater away from the crossbar. The loop defines a cross-point where the ends of the strand cross each other, and the cross-point is preferably positioned radially outside the outer surface of the crossbar. The strand is flexible, and the aperture is sized to permit the loop to travel longitudinally along the strand. The aperture preferably extends a longitudinal distance in the range of about 0.4 mm to about 3.0 mm, while the crossbar typically has a length in the range of about 3.0 mm to about 10.0 mm. The strand may be a metal wire, and is preferably coated with a low-friction material.

Another embodiment of a tissue anchor for connecting a suture to tissue, constructed in accordance with the teachings of the present invention, generally comprises a crossbar and a strand. The crossbar has first and second opposing ends and defines a longitudinal axis. The cross bar is defined by a tubular wall having first and second apertures between the first and second ends, the first and second apertures being longitudinally spaced apart. A flexible suture has first and second opposing ends connected to the first and second opposing ends of the crossbar, respectively. The suture extends through the first and second apertures and projects away from the crossbar between the first and second apertures to define a loop between the suture and the crossbar.

Yet another embodiment of a tissue anchor for connecting a suture to tissue, constructed in accordance with the teachings of the present invention, generally comprises a crossbar and a flange. The crossbar has first and second opposing ends and defines a longitudinal axis. The flange is connected to the crossbar between the first and second ends and extends away from the longitudinal axis. The flange has a thickness less than a diameter of the crossbar. The flange defines a hole sized to receive the suture therein. According to more detailed aspects of this embodiment of the tissue anchor, an outer end surface of the flange follows a curved shape. Preferably, the crossbar and flange are unitarily and integrally formed. The crossbar and flange are optionally molded from a resorbable material.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
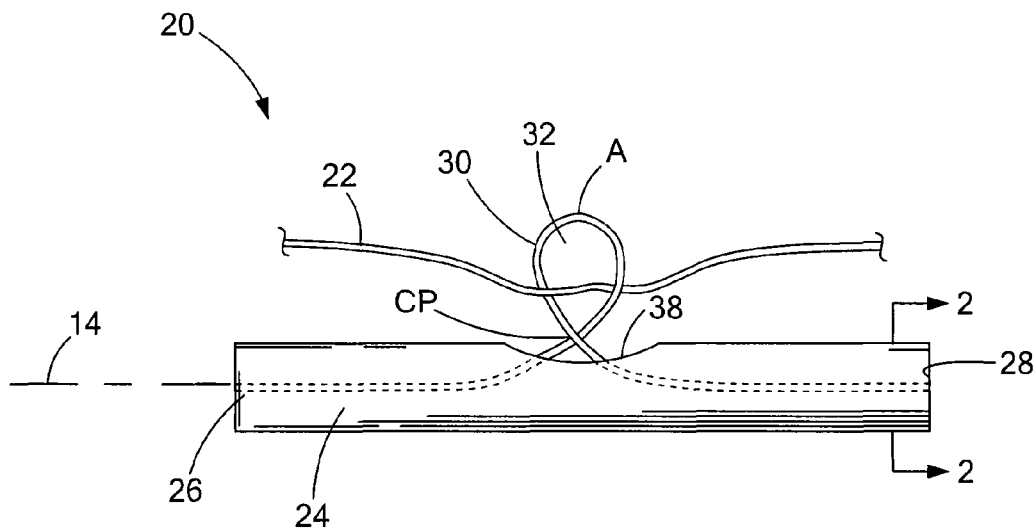
FIG. 1 is a front view of one embodiment of a tissue anchor constructed in accordance with the teachings of the present invention.
Figure 2:
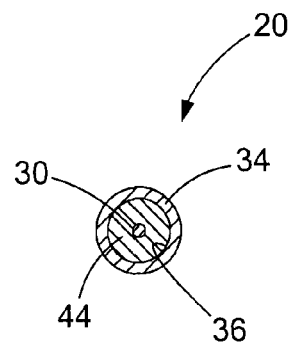
FIG. 2 is a cross-sectional view taken about the line 2-2 in FIG. 1.

Turning now to the figures, FIGS. 1-2 depict a tissue anchor 20 constructed in accordance with the teachings of the present invention. The anchor 20 is utilized to connect a suture 22 to tissue, such as for closing a perforation 10 in a bodily wall 12 (see, e.g., FIGS. 6 to 9) or for use in other procedures. The anchor 20 generally includes a crossbar 24 having opposing ends 26 and 28 and defining a longitudinal axis 14. The crossbar 24 is preferably elongated, but may take any form suitable for connecting the suture 22 to the bodily wall 12. A strand 30 is connected to the crossbar 24 and is configured to form a loop 32. As best seen in FIG. 2, the crossbar 24 is constructed of a cannula having a tubular wall 34 defining a lumen 36. An elongated aperture 38 is formed in the tubular wall 34, and the strand 30 passes through the aperture 38. The ends of strand 30 are secured within the lumen 36 of the cannula by welds 44. It will be recognized by those skilled in the art that the strand 30 may be secured to the crossbar 24 using any now known or hereinafter developed attachment means, including mechanical fasteners, adhesives or various welding or soldering techniques. Similarly, the strand 30 may have sufficient rigidity such that its ends do not need to be directly attached to the crossbar, as the formation of loop 32 projecting through the aperture 38 can be enough to retain the strand 30 within the crossbar 24, and/or the ends of the strand 30 may simply be bent or otherwise deformed to keep them within the crossbar 24 and prevent them from passing through the aperture 38.

The strand 30 is preferably formed from a metal wire, including single filament and multi-filament wires, and wound and braided wires, although the strand 30 can have other constructions such as suture material, plastic strings, rope and the like. As best seen in FIG. 1, the strand 30 is structured to include a revolution thereby defining a loop 32 through which the suture 22 passes. The loop 32 is positioned longitudinally in-line with the elongated aperture 38 so that it projects through the aperture 38 and away from the longitudinal axis 14. Accordingly, it will be seen that the strand 30 and its loop 32 are flexible and may adjust its shape and orientation based on how the suture 22 is being tensioned. The size of the elongated aperture 38 and the flexibility of the strand 30 allow the loop 32 to travel longitudinally along the length of the strand 30. The loop 32 defines an apex A which is preferably located about 0.35 mm or greater away from the crossbar 24. The loop 32 also defines a cross-point CP where the ends of the strand 30 cross each other. The cross-point CP is preferably positioned radially outside the outer surface of the crossbar 24 including radially outside the side walls of the aperture 38, but also preferably as close to the crossbar 24 as possible. The aperture 38 preferably extends a longitudinal distance in a range of about 0.4 mm to about 3.0 mm, while the crossbar 24 typically has a length in the range of about 3.0 mm to about 10.0 mm. The strand preferably has a diameter less than about 50% of a diameter of the crossbar 24, and most preferably less than about 35%. The strand 30 preferably has a diameter in the range of about 0.20 mm to about 0.35 mm, and most preferably about 0.254 mm. The crossbar 24 preferably has a diameter in the range of about 0.5 mm to about 1.0 mm, and most preferably about 0.8 mm. The strand 30 may be coated with a low-friction material such as known plastic or hydrophilic coatings.

This construction of the tissue anchor 24 and its loop 32 allows the suture 22 to be tensioned and slid through the loop 32 relative to the crossbar 24 while preventing the suture 22 from engaging the crossbar 24 or the edges defined by the elongated aperture 38. That is, no matter which direction the ends of the suture 22 are pulled or slid relative to the crossbar 24, the wire 30 and its loop 32 will serve as a barrier between the suture 22 and the canula 24 to prevent any undesired abrasion therebetween. Generally, the strand 30 has a length and the location of the apex A of the loop 32 are such that the loop 32 is sized to project through the tissue in which it is embedded (e.g. it projects from the proximal side of the tissue), allowing reliable tensioning of the suture 22 and preventing abrasion of the tissue.

Figure 3:
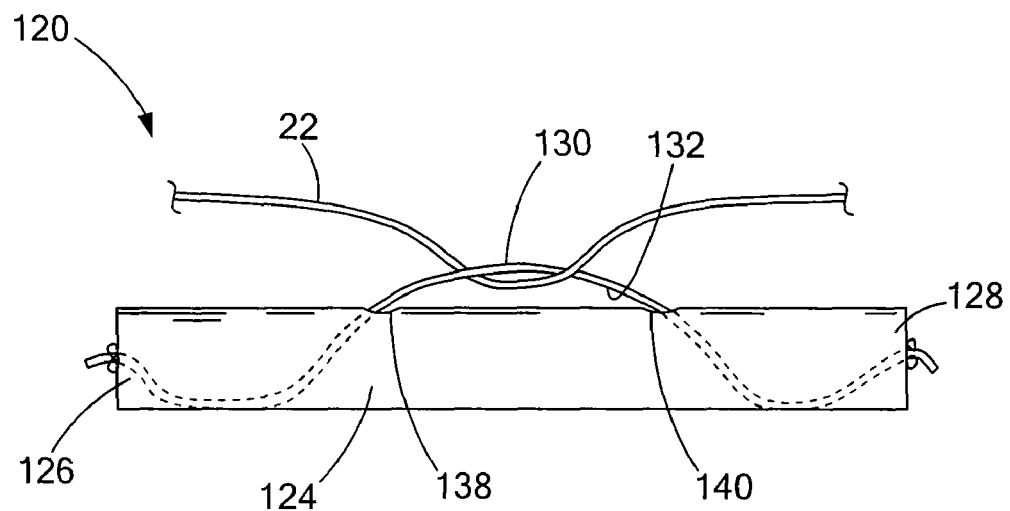
FIG. 3 is a front view of another embodiment of a tissue anchor constructed in accordance with the teachings of the present invention.

Turning now to FIG. 3, another embodiment of a tissue anchor 120 is depicted in accordance with the teachings of the present invention. As in the prior embodiment, the anchor 120 generally includes a crossbar 124 having opposing ends 126 and 128. A strand 130 is connected to the crossbar 124, and in this embodiment, the strand 130 is formed of a flexible suture. The crossbar 24 defines first and second apertures 138, 140 which are longitudinally spaced apart. Moving from left to right in FIG. 3, the strand 130 is attached to the crossbar 124 and passes through the interior of the crossbar 124 and exits radially from the first aperture 138, then extends along the outer periphery of the crossbar 124, and passes back through the second aperture 140 into the interior of the crossbar 124, where it is fixed to the second end 128 thereof. Accordingly, the flexible suture 130 and the crossbar 124 define a loop 132 therebetween which is sized to slidably receive the tying suture 22. The suture 130 has a length, preferably about 10 mm to about 30 mm, such that the distance the suture 130 projects away from the crossbar 124 is variable. The suture 130, when pulled taut, defines an apex that is positioned away from an outer surface of the crossbar about 5 mm. Preferably the suture 130 has a length 18 mm, whereas the crossbar 124 has a length of about 8 mm. The suture 130 may be of a single filament or multi-filament constructions. Through this construction of the suture 130 to form the loop 132, while friction between the anchor 120 and the tying suture 22 is reduced. The loop 132 and with the extra length of the suture 130, the crossbar 124 may be embedded deeper into the tissue.

Figure 4:
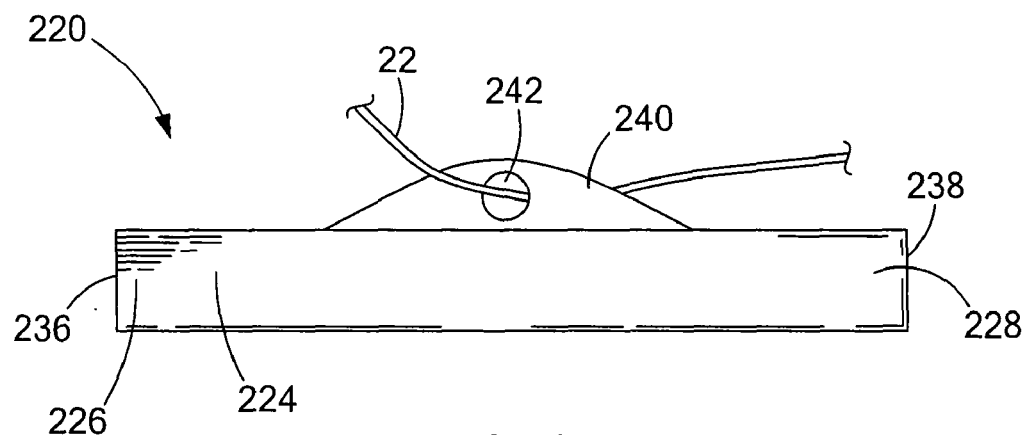
FIG. 4 is a front view of yet another embodiment of a tissue anchor constructed in accordance with the teachings of the present invention.
Figure 5:
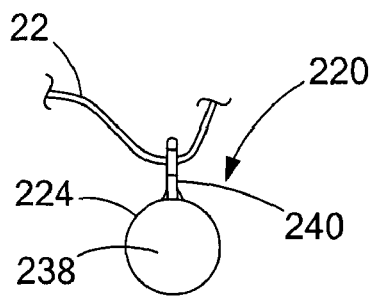
FIG. 5 is an end view taken of the tissue anchor depicted in FIG. 4.

Turning now to FIGS. 4 and 5, in yet another embodiment of a tissue anchor 220 has been depicted in accordance with the teachings of the present invention. As with the prior embodiments the anchor 220 generally includes a crossbar 224 having opposing ends 226 and 228. In this embodiment the crossbar 224 is preferably formed of a solid cylinder, and may be a metal bar, plastic molded piece, or any stock materials. The tissue anchor 220 also includes a flange 240 connected to the crossbar 224 and projecting radially away therefrom. The flange 240 preferably has a thickness (best seen in the side view of FIG. 5) that is less than 50% of the diameter of the crossbar 224. The flange 240 defines a hole 242 sized to slidably receive the tying suture 22 therein. Preferably, the crossbar 224 and flange 240 are unitarily and integrally formed, such as in a plastic molding process. Accordingly, the entire tissue anchor 220 may be formed of a single plastic material, and most preferably a resorbable material. This construction of the tissue anchor 220 allows it to be placed in locations where, once the anchor was freed, it would likely not naturally pass through the body. Accordingly, no matter the location the tissue anchors 220, they are still allowed to naturally exit the body.

As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; tri-methlyene carbonate; polycaprolactone; poly-beta hydroxy acids such as polyhydroxybutyrate or polyhydroxyvalerate; or other polymers such as polyphosphazines, polyorgano-phosphazines, polyanhydrides, polyesteramides, poly-orthoesters, polyethylene oxide, polyester-ethers (e.g., poly-dioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Figure 6:
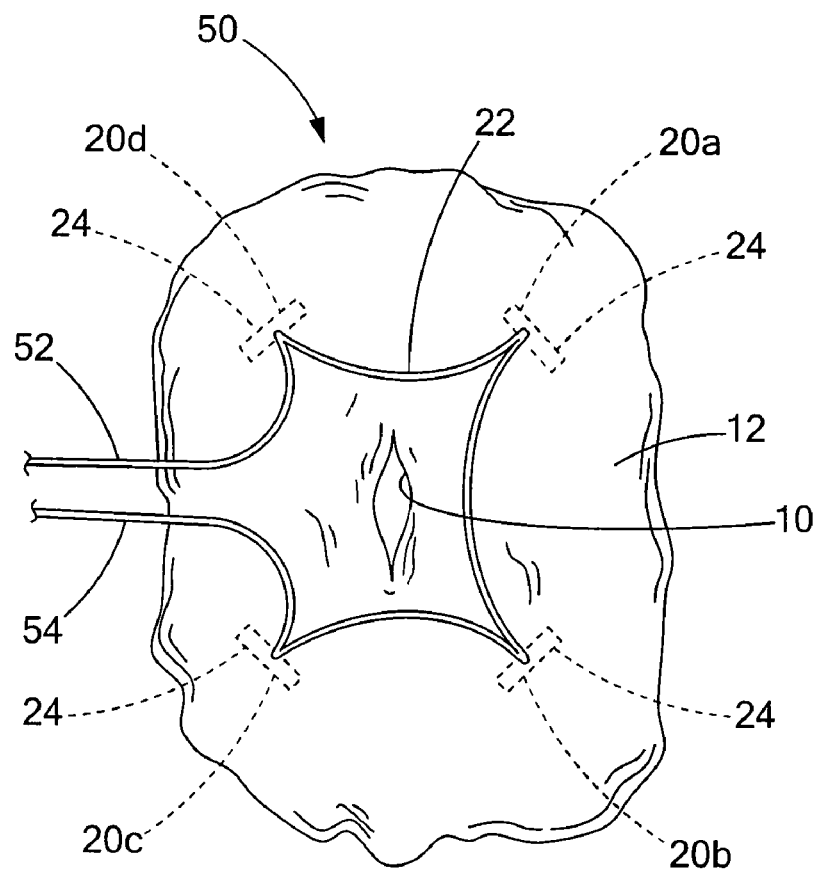
FIG. 6 is a plan view schematically depicting a medical device constructed in accordance with the teachings of the present invention.
Figure 7:
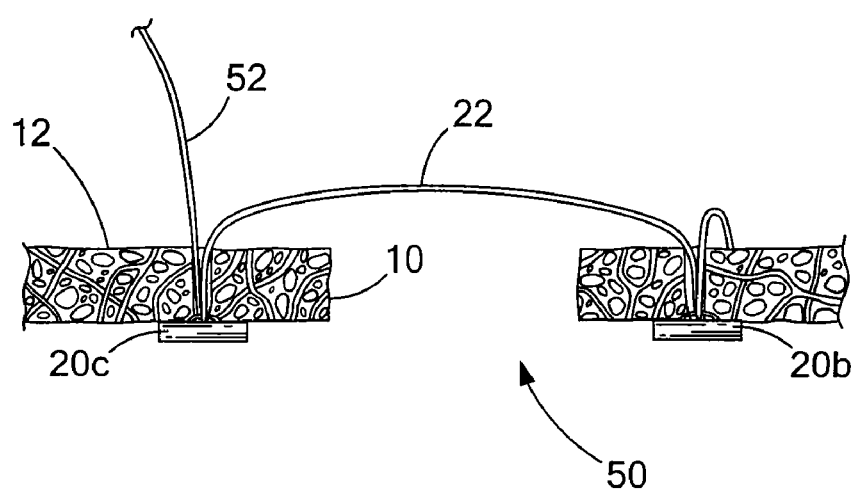
FIG. 7 is a cross-sectional view of the medical device depicted in FIG. 6.

Turning now to FIGS. 6-9, the tissue anchors 20 are preferably deployed as a set of anchors 20a, 20b, 20c, 20d linked together by a single suture 22, all of which collectively forms a medical device 50 for closing the perforation 10 in the bodily wall 12. The suture 22 is slidably connected to each of the tissue anchors 20a, 20b, 20c, and 20d, leaving two free ends 52, 54 of the suture 22 which may be independently tensioned to close the perforation 10. As best seen in FIG. 7, the tissue anchors (20b and 20c depicted) are positioned on a distal side of the bodily wall 12, while the majority of suture 22 is positioned on a proximal side of the bodily wall 12, including the suture ends 52, 54. Accordingly, it will be recognized that the medical device 50 operates in a pursestring fashion to close the perforation 10 in the bodily wall, as will be described in more detail below.

Figure 8:
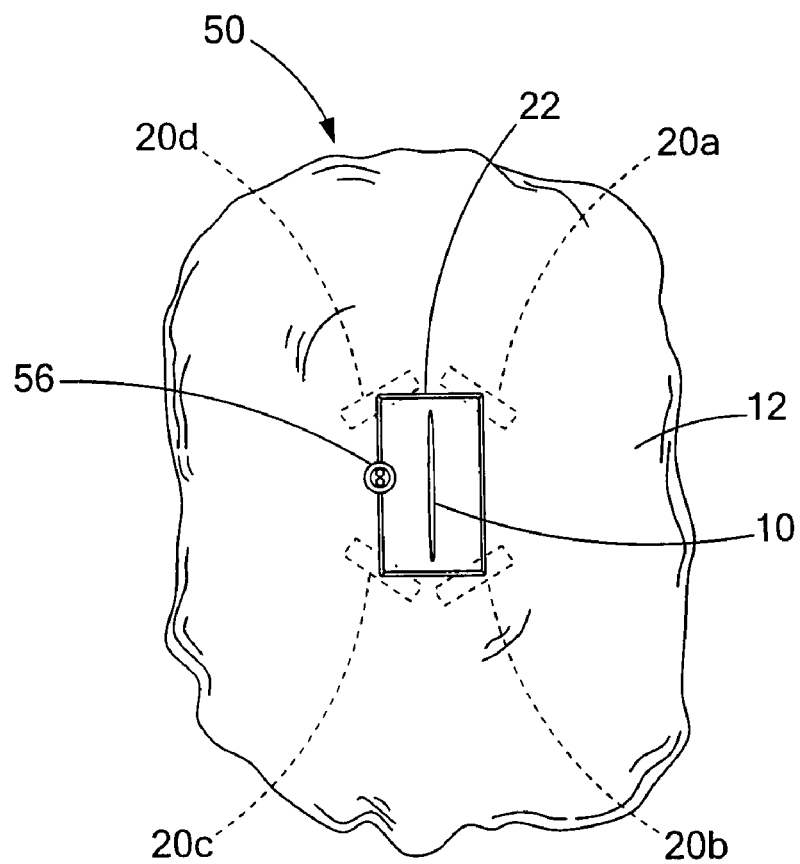
FIG. 8 is a schematic view of the medical device similar to FIG. 6 but showing the medical device closing a perforation.
Figure 9:
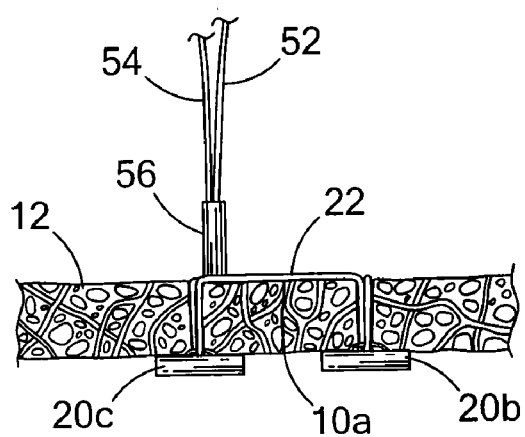
FIG. 9 is a cross-sectional view of the medical device as depicted in FIG. 8.

A method of closing the perforation 10, in accordance with the teachings present invention, includes passing each tissue anchor 20a, 20b, 20c, and 20d through the bodily wall 12 adjacent the periphery of the perforation 10, as shown in FIG. 6. Preferably, the anchors are sequentially positioned around the perforation 10 in a semi-annular or annular shape as shown. The ends 52, 54 of the suture are then tensioned to reduce the distance between the tissue anchors 20a, 20b, 20c, 20d and compress the bodily wall 12 around the perforation 10, as depicted in FIGS. 8 and 9. As best seen in FIG. 9, the ends 52, 54 of the suture 22 are secured to maintain the compression of the bodily wall 10, such as through the use of a suture lock 56. Exemplary suture locks are disclosed in copending U.S. patent application Ser. Nos. 12/125,525 and 12/191,001, the disclosures of which are incorporated herein by reference in their entirety. It will be recognized that any now known or future developed method for securing the ends 52, 54 of the suture 22 may be employed, such as knotting, tying, clamps, rivets and the like.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A tissue anchor for connecting a suture to tissue, the tissue anchor comprising: a crossbar having first and second ends and defining a longitudinal axis therebetween, the crossbar being defined by a tubular wall having an aperture between the first and second ends; and a strand having first and second ends connected to the first and second ends of the crossbar, respectively, the strand making a revolution to define a loop, the strand and its loop projecting through the aperture and away from the longitudinal axis, the loop sized to slidably receive the suture therein, wherein the loop defines a crosspoint where the strand crosses itself, the cross-point spaced longitudinally away from the first and second ends of the strand; wherein the tubular wall defines a lumen extending longitudinally, and the aperture communicates the lumen with an outer surface of the crossbar, the strand extends from its first end longitudinally through the lumen, through the aperture, makes the loop, back through the aperture, and again longitudinally through the lumen to its second end, wherein the first and second ends of the strand are immovably fixed to the crossbar.

2. The tissue anchor of claim 1, wherein the strand has a diameter less than about 35% of a diameter of the crossbar.

3. The tissue anchor of claim 1, wherein the strand has a diameter in the range of about 0.20 mm to about 0.35 mm.

4. The tissue anchor of claim 1, wherein the crossbar has a diameter in the range of about 0.5 mm to about 1.0 mm.

5. The tissue anchor of claim 1, wherein the loop has an apex located about 0.35 mm away from the crossbar.

6. The tissue anchor of claim 1, wherein the cross-point is positioned radially outside the outer surface of the crossbar.

7. The tissue anchor of claim 1, wherein the strand is flexible, and wherein the aperture is sized to permit the loop to travel longitudinally along the strand.

8. The tissue anchor of claim 1, wherein the aperture extends a longitudinal distance in the range of about 1.0 mm to about 3.0 mm.

9. The tissue anchor of claim 1, wherein the strand is a metal wire.

10. The tissue anchor of claim 1, wherein the strand is coated with a low-friction material.

11. The tissue anchor of claim 1, wherein the first and second ends of the strand are directly connected to the ends of the crossbar using one or more of adhesives, welds or solder.

12. The tissue anchor of claim 1, wherein the strand terminates at its first and second ends adjacent the first and second ends of the crossbar.

* * * * *